(12) United States Patent
Fadem

(10) Patent No.: US 9,072,448 B2
(45) Date of Patent: *Jul. 7, 2015

(54) ELECTRODE SYSTEM WITH RIGID-FLEX CIRCUIT

(71) Applicant: Neuronetrix Solutions, LLC, Louisville, KY (US)

(72) Inventor: Kalford C. Fadem, Louisville, KY (US)

(73) Assignee: Neuronetrix, Solutions, LLC, Louisville, KY (US)

( * ) Notice: Subject to any disclaimer, the term of this patent is extended or adjusted under 35 U.S.C. 154(b) by 47 days.

This patent is subject to a terminal disclaimer.

(21) Appl. No.: 13/897,900

(22) Filed: May 20, 2013

(65) Prior Publication Data

US 2013/0253300 A1 Sep. 26, 2013

Related U.S. Application Data

(63) Continuation of application No. 13/428,183, filed on Mar. 23, 2012, now Pat. No. 8,463,354, which is a continuation of application No. PCT/US2010/049973, filed on Sep. 23, 2010.

(60) Provisional application No. 61/245,686, filed on Sep. 25, 2009.

(51) Int. Cl.
*A61B 5/0478* (2006.01)
*A61B 5/0484* (2006.01)
*A61B 5/00* (2006.01)

(52) U.S. Cl.
CPC ......... *A61B 5/0484* (2013.01); *A61B 2562/166* (2013.01); *A61B 2560/0443* (2013.01);
(Continued)

(58) Field of Classification Search
CPC ............. A61B 5/04004; A61B 5/0476; A61B 5/0478; A61B 5/0482; A61B 5/0484–5/04847;
A61B 5/0464; A61B 5/4076; A61B 5/4094; A61B 5/6803; A61B 5/6814; A61B 5/6831; A61B 2560/04; A61B 2560/0443; A61B 2562/0209; A61B 2562/125; A61B 2562/16; A61B 2562/166; A61B 2562/22; A61B 2562/227
USPC .................................. 600/383, 393, 544, 545
See application file for complete search history.

(56) References Cited

U.S. PATENT DOCUMENTS 4,967,038 A 10/1990 Gevins et al.
5,479,934 A 1/1996 Imran
(Continued)

FOREIGN PATENT DOCUMENTS

JP H09-108195 4/1997
JP 2009-530064 8/2009
(Continued)

OTHER PUBLICATIONS

International Search Report and Written Opinion dated Dec. 6, 2010 for PCT/US2010/049973.
(Continued)

*Primary Examiner* — Lee S Cohen
*Assistant Examiner* — Erin M Cardinal
(74) *Attorney, Agent, or Firm* — Frost Brown Todd LLC

(57) ABSTRACT

An electrode system comprises a flexible circuit substrate, a plurality of electrode modules, and a plurality of sensors. The flexible circuit substrate comprises a flexible material and traces supported by the flexible material. The flexible circuit substrate extends through at least two of the electrode modules such that the electrode modules encompass portions of the flexible circuit substrate. Each electrode module comprises at least one rigid circuit member configured to process ERPs of a test subject. The rigid circuit members are layered against the flexible circuit substrate such that the rigid circuit members and the flexible circuit substrate together form a rigid-flex circuit. The sensors may be removably coupled with at least one of the plurality of electrode modules and may sense ERPs from the test subject.

18 Claims, 9 Drawing Sheets

(52) U.S. Cl.
CPC ....... *A61B5/6814* (2013.01); *A61B 2562/0209* (2013.01); *A61B 2562/046* (2013.01); *A61B 2562/164* (2013.01); *A61B 5/0478* (2013.01)

(56) References Cited

U.S. PATENT DOCUMENTS

| | | | |
|---|---|---|---|
| 6,115,623 | A | 9/2000 | McFee |
| 6,381,481 | B1 | 4/2002 | Levendowski et al. |
| 7,130,673 | B2 | 10/2006 | Tolvanen-Laakso et al. |
| 7,378,596 | B2 | 5/2008 | Kawaguchi et al. |
| 7,618,260 | B2 | 11/2009 | Daniel et al. |
| 8,112,141 | B2 | 2/2012 | Wilson et al. |
| 8,364,238 | B2 * | 1/2013 | Fadem ........................ 600/383 |
| 8,463,354 | B2 * | 6/2013 | Fadem ........................ 600/383 |
| 2005/0215916 | A1 | 9/2005 | Fadem et al. |
| 2007/0106169 | A1 | 5/2007 | Fadem |
| 2007/0191727 | A1 | 8/2007 | Fadem |
| 2007/0225585 | A1 | 9/2007 | Washbon et al. |
| 2007/0270678 | A1 | 11/2007 | Fadem et al. |
| 2008/0208072 | A1 | 8/2008 | Fadem et al. |
| 2009/0105576 | A1 | 4/2009 | Do et al. |
| 2009/0306485 | A1 | 12/2009 | Bell |

FOREIGN PATENT DOCUMENTS

| | | |
|---|---|---|
| WO | WO 2007/109745 | 9/2007 |
| WO | WO 2010/056947 | 5/2010 |

OTHER PUBLICATIONS

U.S. Appl. No. 61/381,569, filed Sep. 10, 2010.
U.S. Appl. No. 61/245,686, filed Sep. 25, 2009.
U.S. Appl. No. 61/381,737, filed Sep. 10, 2010.
Chinese Office Action dated Apr. 22, 2014 for Application No. 2012-531028.

* cited by examiner

ELECTRODE SYSTEM WITH RIGID-FLEX CIRCUIT

PRIORITY

This application is a continuation of application Ser. No. 13/428,183, filed Mar. 23, 2012, entitled "Electrode System with Rigid-Flex Circuit," which issued as U.S. Pat. No. 8,463,354 on Jun. 11, 2013, which is a continuation of PCT International Application No. PCT/US2010/049973, filed Sep. 23, 2010, entitled "Electrode System with Rigid-Flex Circuit," which claims priority to U.S. Provisional Patent Application Ser. No. 61/245,686, filed Sep. 25, 2009, entitled "Electrode System with Rigid-Flex Circuit," the disclosures of which are incorporated by reference herein.

BACKGROUND

In some settings, it may be desirable to position a headset with electrodes on a test subject's head, such as to test the subject for various conditions, including but not limited to various types of diseases or conditions within the cerebral cortex, Alzheimer's, Parkinson's, dyslexia, autism, and/or schizophrenia, among other conditions. For instance, one or more system components may be used to provide one or more types of stimuli to the test subject (e.g., auditory, visual, and/or tactile stimulus, etc.); and electrodes may be used to detect Evoked Response Potentials (ERP's) associated with such stimuli. By way of example only, active or locally amplified electrodes, as well as related systems and methods, are discussed in the following documents, each of which is incorporated by reference herein: U.S. Pat. No. 5,479,934, entitled "EEG Headpiece with Disposable Electrodes and Apparatus and System and Method for Use Therewith," issued Jan. 2, 1996; U.S. Pub. No. 2005/0215916, entitled "Active, Multiplexed Digital Electrodes for EEG, ECG, and EMG Applications," published Sep. 29, 2005; U.S. Pub. No. 2007/0106169, entitled "Method and System for an Automated E.E.G. System for Auditory Evoked Responses," published May 10, 2007; U.S. Pub. No. 2007/0270678, entitled "Wireless Electrode for Biopotential Measurement," published Nov. 22, 2007; U.S. Pub. No. 2007/0191727, entitled "Evoked Response Testing System for Neurological Disorders," published Aug. 16, 2007; and International Pub. No. WO 2010/056947, entitled "Electrode System," published May 20, 2010. It should be understood that the teachings herein may be applied to or otherwise combined with any of the systems and methods taught in all of the above-cited documents. Various suitable ways in which the teachings herein may be combined with teachings in any of the above-cited documents will be apparent to those of ordinary skill in the art.

While a variety of electrode systems have been made and used, and while a variety of methods have been used to construct such electrode systems, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
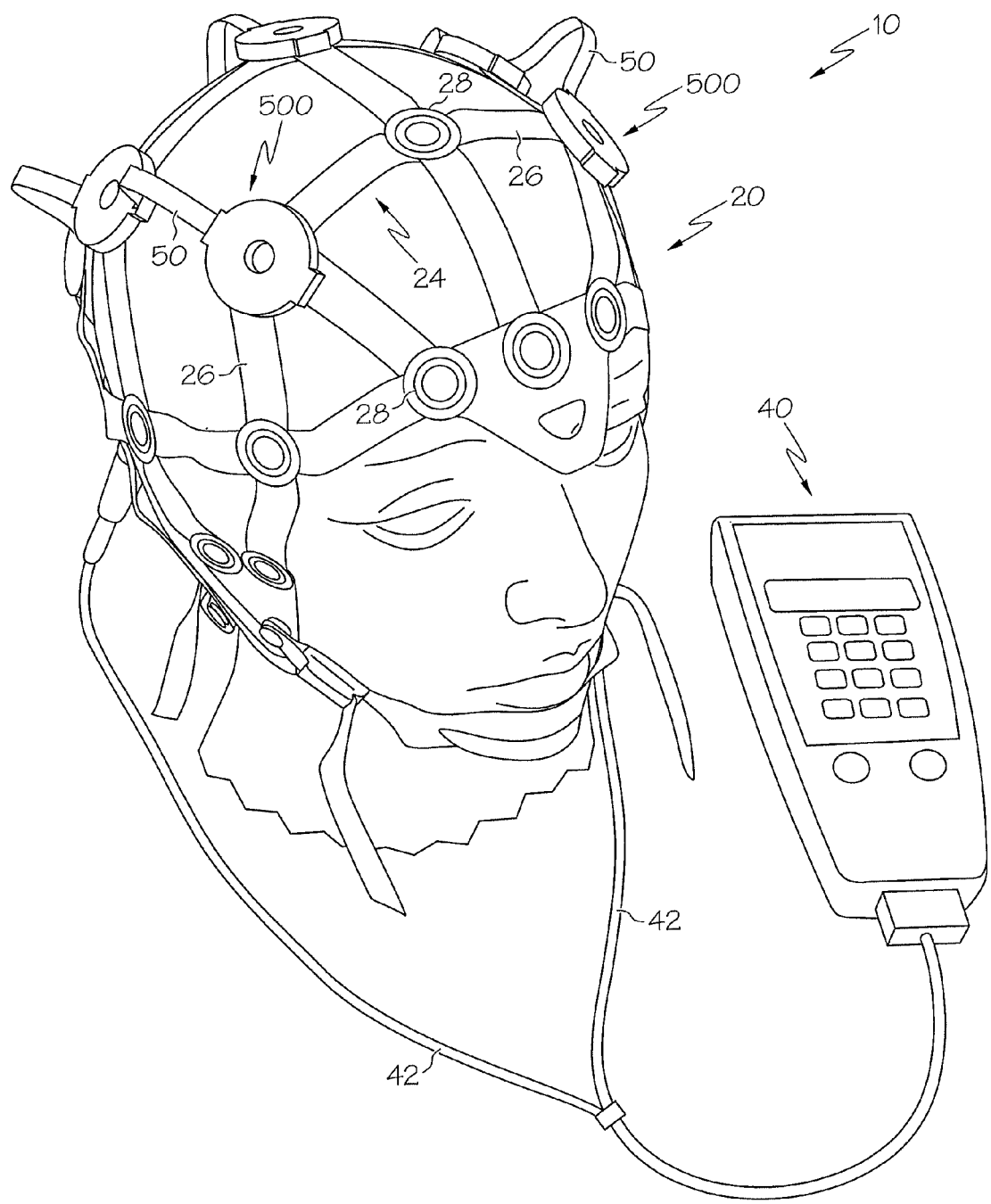
FIG. 1 depicts a perspective view of an exemplary ERP testing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Exemplary System Overview

Figure 2:
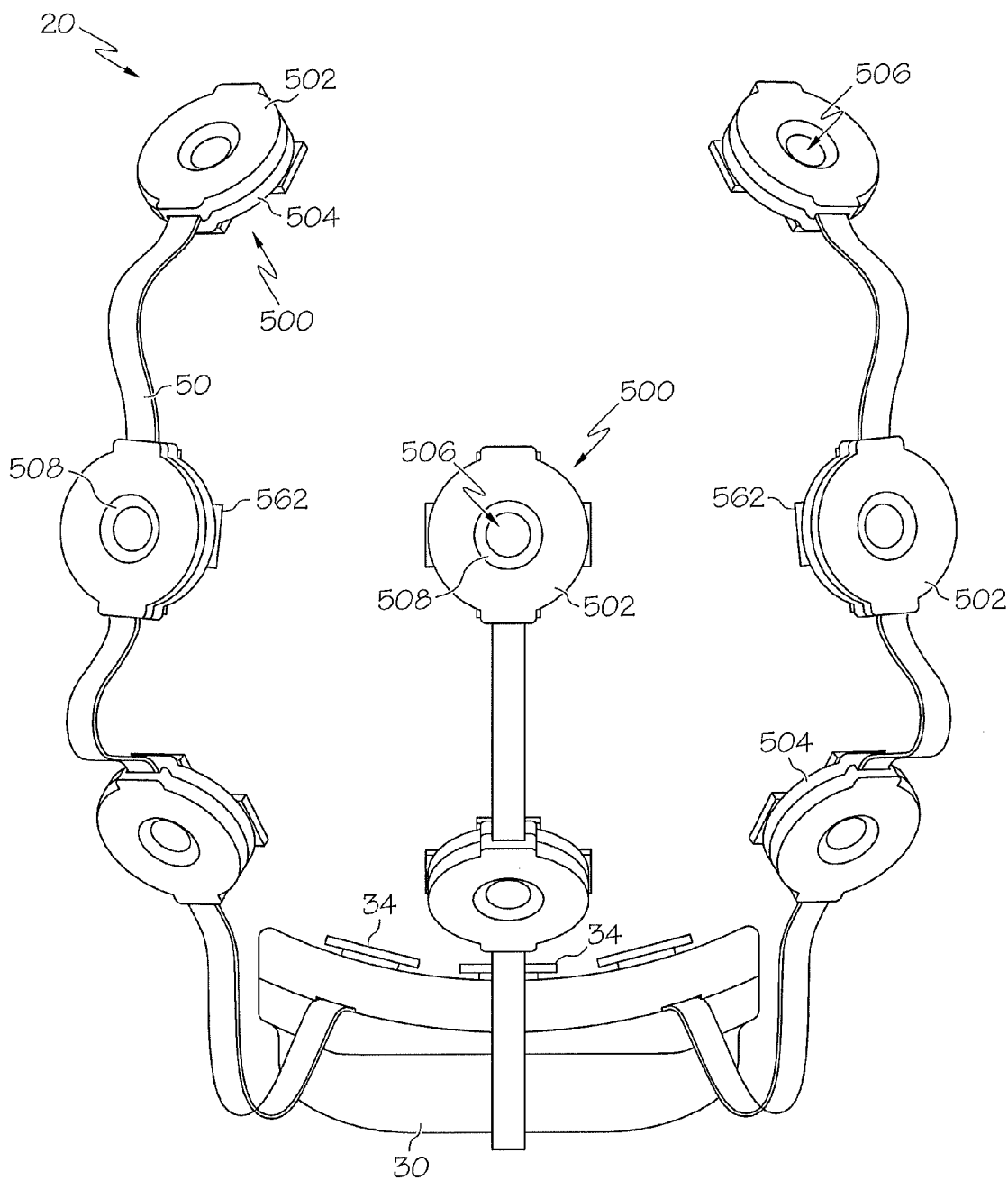
FIG. 2 depicts a top plan view of electrode components of the ERP testing system of FIG. 1.
Figure 3:
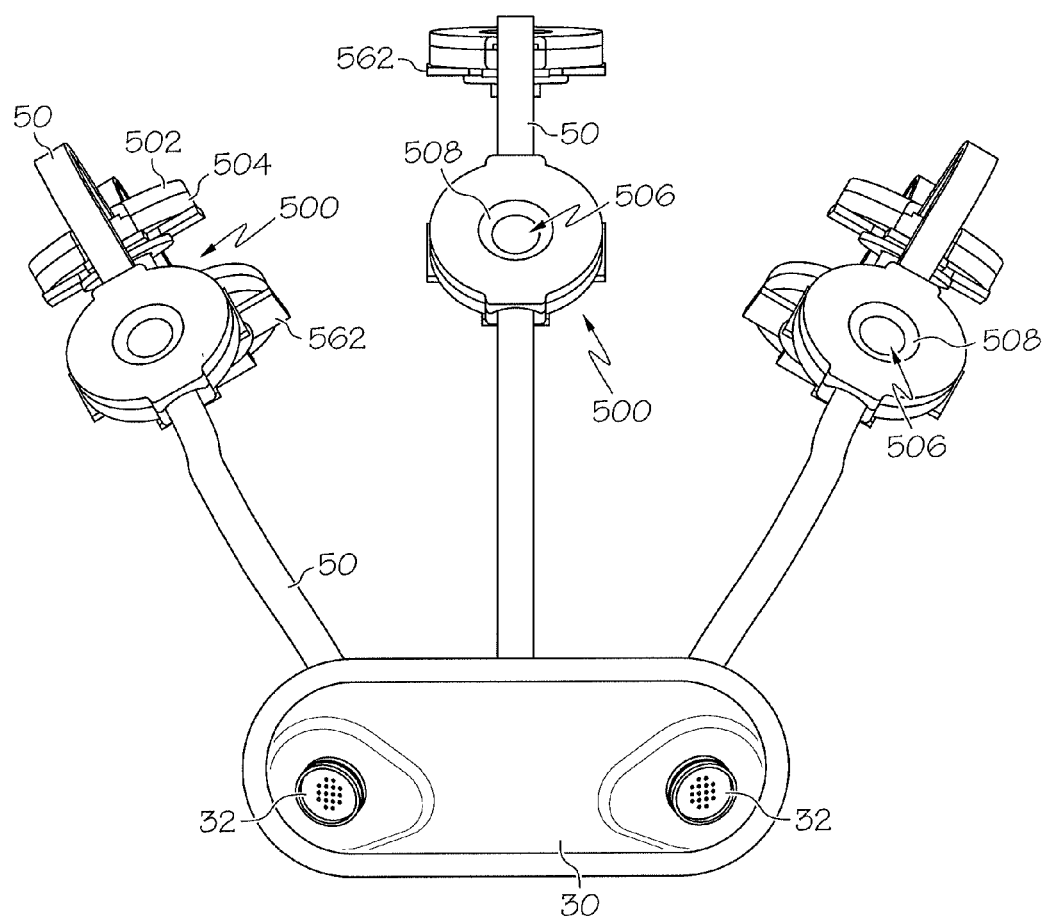
FIG. 3 depicts a rear elevational view of the electrode components of FIG. 2.

As shown in FIG. 1, an exemplary electrode system (10) includes a headset (20) and a control box (40). Headset (20) comprises a head frame (24) and a plurality of electrode modules (500). While headset (20) of the present example comprises eight electrode modules (500), it should be understood that any other suitable number of electrode modules (500) may be used. It should also be understood that the arrangement of electrode modules (500) shown in FIGS. 1-3 is merely exemplary; and that electrode modules (500) may be positioned in any other suitable arrangement. Electrode modules (500) are removably coupled with head frame (24) as will be described in greater detail below.

Exemplary Head Frame

In the example shown in FIG. 1, head frame (24) is formed of several resilient straps (26), and electrode modules (500) are removably secured to head frame (24) at junctions of resilient straps (26). The junctions of resilient straps (26) comprise annular snap members (28), which are each open at their center. As will be described in greater detail below, openings (506) of electrode modules (500) are configured to align with the open centers of corresponding snap members (28), to allow inserted sensors (150) to contact the test subject's head. In some versions, resilient straps (26) are formed of elastic, though it should be understood that any other suitable material or combination of materials may be used. While head frame (24) of the present example is configured to substantially encompass a test subject's head, it should also be understood that head frame (24) may have any other suitable configuration. By way of example only, head frame (24) may comprise a EzeNet® reusable head piece by HydroDot, Inc. of Westford, Mass. A EzeNet® reusable head piece may come in various sizes and conform to the international 10/20 system of electrode placement.

As another merely illustrative example, head frame (24) may be configured and/or operable in accordance with the teachings of U.S. Pub. No. 2007/0191727, entitled "Evoked Response Testing System for Neurological Disorders," published Aug. 16, 2007, the disclosure of which is incorporated by reference herein; and/or in accordance with the teachings of any other document cited herein. Indeed, various ways in which the teachings herein may be combined with the teachings of U.S. Pub. No. 2007/0191727 and/or the teachings of any other document cited herein will be apparent to those of ordinary skill in the art. Alternatively, head frame (24) may have any other suitable configuration and/or operability. Other suitable variations of head frame (24) will be apparent to those of ordinary skill in the art in view of the teachings herein.

As shown in FIGS. 1-3, electrode modules (500) are physically and communicatively coupled with each other via flexible connectors (50). Electrode modules (500) are also physically and communicatively coupled with a control box interface module (30) via flexible connectors (50). Flexible connectors (50) of the present example comprise flexible circuits, which comprise traces (not shown) formed in a flexible substrate. Alternatively, conventional wires or other conduits may be used. In the present example, headset (20) is coupled with control box (40) via cables (42). In particular, control box interface module (30) includes ports (32), with which cables (42) may be coupled. Control box interface module (30) also includes circuitry configured to route signals between flexible connectors (50) and cables (42) via ports (32). Control box interface module (30) may thus provide a communicative interface between cables (42) and flexible connectors (50). Various suitable components that may be incorporated into control box interface module (30), as well as various suitable features/functionalities of such components, are described in the documents cited herein. By way of example only, control box interface module (30) may be constructed and operable in accordance with the headset "control module 12" teachings of U.S. Pub. No. 2007/0191727 and/or the teachings of any other document cited herein. Still other suitable components that may be incorporated into control box interface module (30) will be apparent to those of ordinary skill in the art in view of the teachings herein.

In the present example, and as shown in FIG. 2, control box interface module (30) also includes flanged members (34). Flange members (34) are configured to secure control box interface module (30) with head frame (24). For instance, head frame (24) may include openings that are configured to receive flanged members (34). Of course, control box interface module (30) may be secured to head frame (24) in a variety of other ways as will be appreciated by those of ordinary skill in the art, to the extent that control box interface module (30) is secured to head frame (24) at all. Furthermore, control box interface module (30) may simply be omitted in some versions (e.g., cables (42) couple directly to freely hanging flexible connectors (50), etc.).

Electrode modules (500) may be coupled with head frame (24) in a variety of ways. In the present example, electrode modules (500) are coupled with head frame (24) through snap fittings at snap members (28) of head frame (24). For instance, electrode modules (500) may be removably coupled with head frame in accordance with the teachings of U.S. Pub. No. 2010/0125190, entitled "Electrode System," published May 20, 2010, the disclosure of which is incorporated by reference herein. Alternatively, electrode modules may be coupled with head frame (24) in any other suitable fashion.

Figure 4:
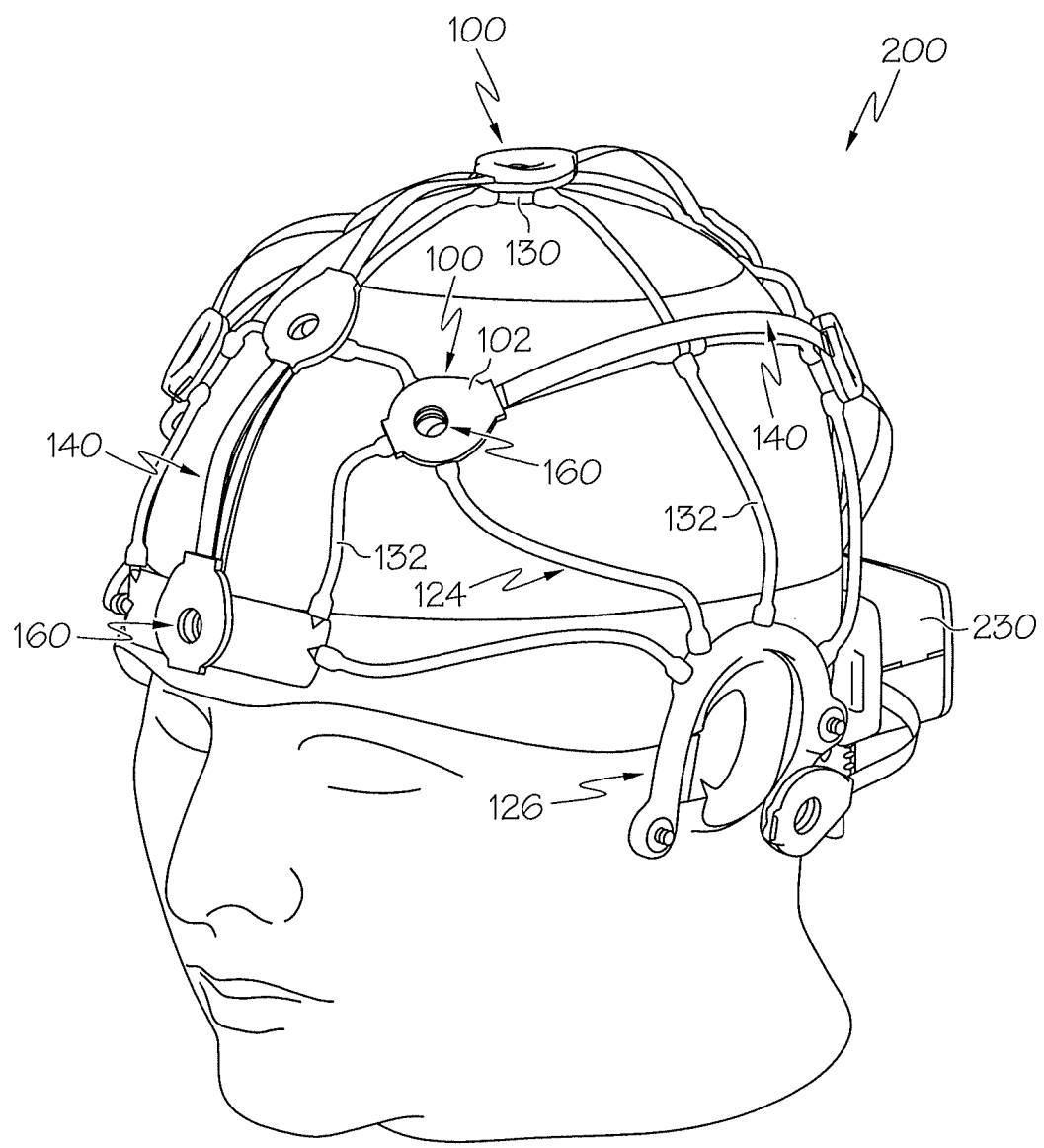
FIG. 4 depicts a perspective view of another exemplary ERP testing system.

An exemplary alternative head frame (124) is shown in FIG. 4, which depicts exemplary alternative headset (200). Unless otherwise described herein, headset (20) and headset (200) are substantially similar in the present example, such that headset (200) may be readily incorporated into electrode system (10) in place of headset (20). Head frame (124) of this example comprises resilient straps (132), which are joined together at frame mounts (130). As described in greater detail below, electrode modules (100) are removably secured to head frame (124) at frame mounts (130). As will also be described in greater detail below, electrode modules (100) and frame mounts (130) define complementary openings permitting insertion of sensors (150) to establish sensory contact with the test subject for reception of ERP signals. In some versions, resilient straps (132) are formed of silicone rubber, though it should be understood that any other suitable material or combination of materials may be used. Head frame (124) also includes framework (126) for removably receiving headphone speakers (not shown), which may be used during audiometry testing, ERP testing, and/or other kinds of testing. Various suitable ways in which audio may be incorporated into various kinds of testing are disclosed in at least some of the references that are cited and incorporated by reference herein. While head frame (124) of the present example is configured to substantially encompass a test subject's head, it should also be understood that head frame (124) may have any other suitable configuration. Various other suitable ways in which head frames (24, 124) may be configured will be apparent to those of ordinary skill in the art in view of the teachings herein.

Exemplary Control Box

While control box (40) is only shown with headset (20) in FIG. 1, it should be understood that control box (40) may also be readily used with headset (200) shown in FIG. 4. Control box (40) of the present example includes a storage medium (not shown) that is configured to store various testing protocols (e.g., ERP testing protocols, etc.); and a processor (not shown) that is configured to execute such testing via headset (20). In particular, control box (40) provides power and commands or other types of signals to headset (20, 200) via cables (42) in the present example; while headset (20, 200) transmits data or other types of signals back to control box (40) via cables (42). Control box (40) is also operable to store data collected during such testing, including but not limited to data obtained through electrode modules (100, 500). Such power, commands, data, or other types of signals may be provided in accordance with various types of ERP testing protocols as described herein and as described in the documents that are incorporated by reference herein.

Control box (40) is configured to be coupled with a computer system (not shown) via wire and/or wirelessly. For instance, a computer system may transmit testing protocols, commands, or other data to control box (40). Similarly, control box (40) may transmit commands, test results, or other data to a computer system. Control box (40) of the present example is also configured to be handheld (e.g., held in a single hand of a person). By way of example only, control box (40) may be held in the hand of the test subject who is wearing headset (40), in the hand of a clinician or nurse, or in the hand of any other person. In addition to or in lieu of the foregoing, control box (40) may be configured in accordance with, operable in accordance with, and/or possess any suitable features/functionalities of similar components described in any of the documents cited herein, including but not limited to U.S. Pub. No. 2007/0191727. Various ways in which the teachings herein may be incorporated into or otherwise combined with the teachings of the documents that are cited herein will be readily apparent to those of ordinary skill in the art.

While two cables (42) are shown, it should be understood that just one cable (42) may be used. It should also be understood that some other versions of electrode system (10) may provide communication of power, commands, data, and/or other types of signals to and/or from headset (20, 200) wirelessly, in addition to or in lieu of having cables (42).

Exemplary Electrode Module

In the example shown in FIGS. 1-3, electrode modules (500) of headset (20) are substantially identical to each other. Each electrode module (500) comprises an upper clamshell member (502), a lower clamshell member (504), a central opening (506) with adjacent inclined surface (508), and mount tabs (562). Additional details regarding the construction and functionality of electrode modules (500) may be found in of U.S. Pub. No. 2010/0125190, entitled "Electrode System," published May 20, 2010, the disclosure of which is incorporated by reference herein.

In the example shown in FIG. 4, electrode modules (100) of headset (200) are also substantially identical to each other. The following description will therefore just describe an individual electrode module (100) as an example. It should be understood, however, that a given electrode system (10) may have different types of electrode modules (100, 500). In other words, one or more electrode modules (100, 500) within a given electrode system (10) may have features, components, functionalities, etc., that differ from the features, components, functionalities, etc., of other electrode modules (100, 500) within the same electrode system (10). Such differences among electrode modules (100, 500) may be based on a variety of considerations, including but not limited to the location of electrode module (100, 500) on the test subject's head or other part of the test subject's anatomy. Suitable ways in which electrode modules (100, 500) may differ from each other within a given electrode system (10) will be apparent to those of ordinary skill in the art in view of the teachings herein. Alternatively, as in the present example, all electrode modules (100, 500) within a given electrode system (10) may be substantially identical to each other.

It should also be understood that electrode modules (500) are different from electrode modules (100) in the present example. In particular, electrode modules (500) comprise rigid circuits that are separately formed and coupled with separate discrete pieces of flexible connectors/circuitry (50); whereas electrode modules (100) comprise a unitary rigid-flex circuit (110), with a single flexible circuit (140) being shared by and common to several electrode modules (100) as described in greater detail below.

Figure 5:
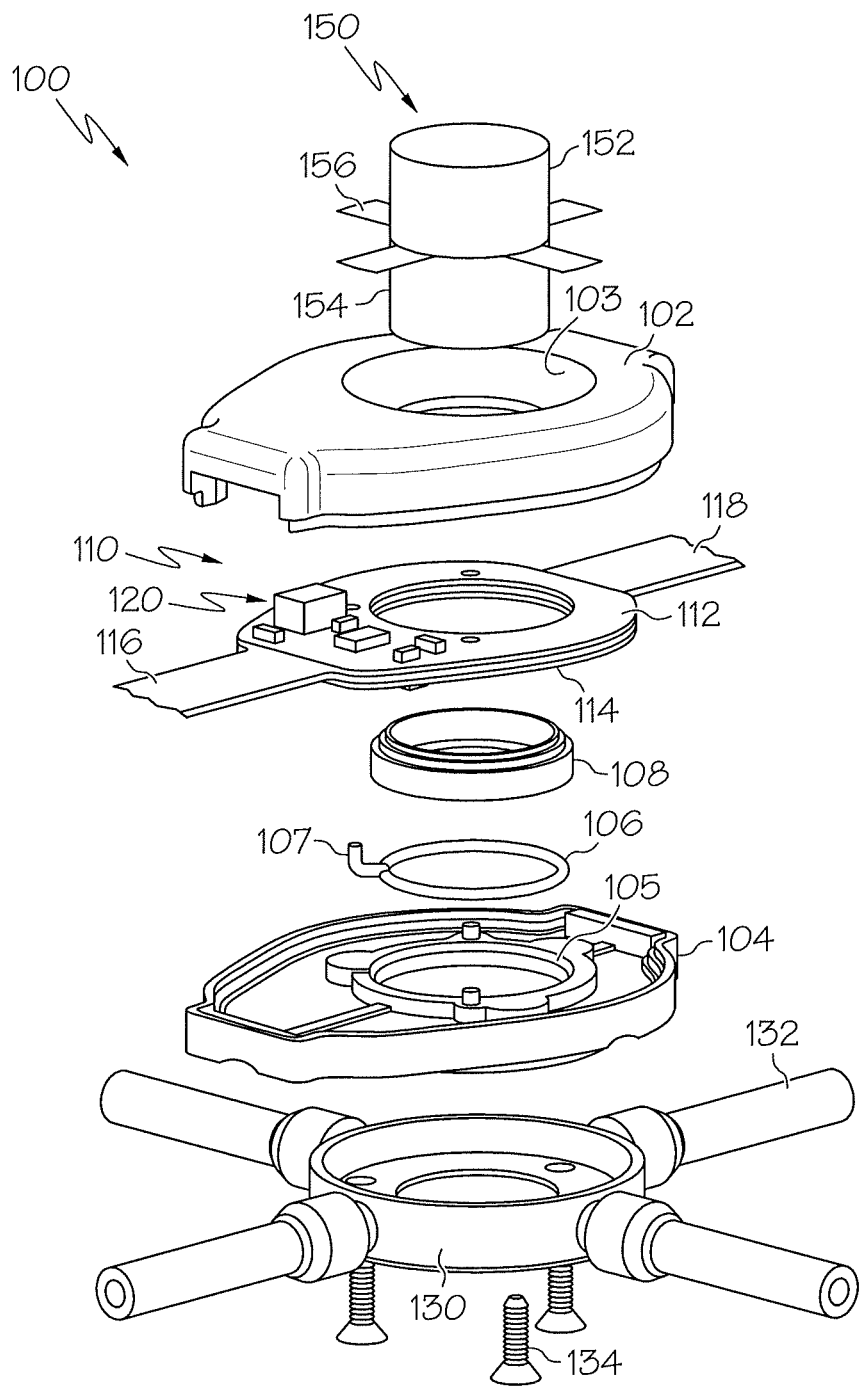
FIG. 5 depicts an exploded perspective view of an electrode module and associated components of the ERP testing system of FIG. 4.
Figure 6:
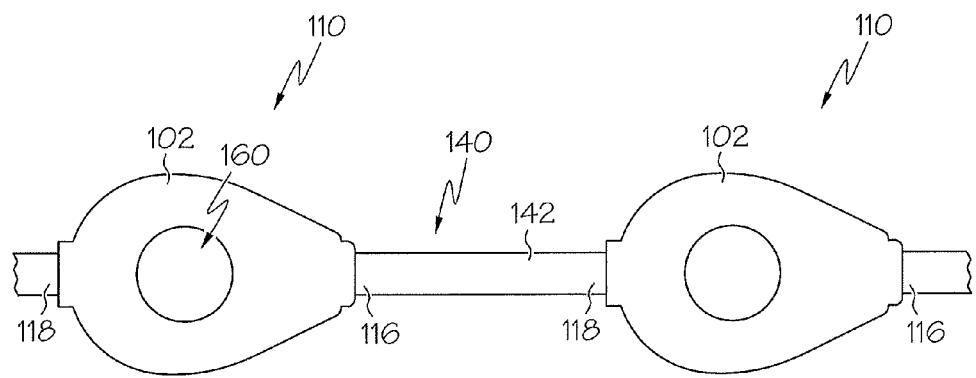
FIG. 6 depicts a top plan view of electrode components of the ERP testing system of FIG. 4.

As shown in FIG. 5, electrode module (100) of this example comprises an upper clamshell member (102), a lower clamshell member (104), a conductive ring (106), a capture ring (108), and a rigid-flex circuit (110). As best seen in FIGS. 4 and 6, upper clamshell member (102), lower clamshell member (104), conductive ring (106), capture ring (108), and rigid-flex circuit (110) all define a central opening (160). In particular, the central openings of upper clamshell member (102), lower clamshell member (104), circuit board (130), and conductive ring (106) are all configured to coaxially align when these components are assembled together to form electrode module (100), such that the assembled electrode module (100) itself defines a central opening (160). This central opening (160) is configured to insertingly receive a sensor (150) as will be described in greater detail below. In addition, these components are configured such that a portion of conductive ring (106) is exposed in the inner diameter of central opening (160) of the assembled electrode module (100), as will also be described in greater detail below. During assembly of electrode module (100), upper clamshell member (102) may be secured to lower clamshell member (104) using any suitable technique or techniques, including but not limited to ultrasonic welding, snap-fitting, adhesives, fasteners, etc. While opening (160) is at the approximate center of electrode module (100) in the present example, it should be understood that opening (160) may be located off-center or otherwise relative to the remainder of electrode module (100).

FIG. 5 also shows a frame mount (130) and resilient straps (132) coupled with frame mount (130). Electrode module (100) may be secured to frame mount (130) via fasteners (134) or in any other suitable fashion (e.g., adhesive, snap-fitting, etc.) It should be understood that resilient straps (132) may connect several frame mounts (130) in an array, such as to form head frame (124). Resilient straps (132) may thus be analogized to the resilient straps (26) shown in FIG. 1 and described above. In some other versions, resilient straps (132) are secured directly to electrode modules (100), such that frame mounts (130) may be eliminated. It should be understood, however, that when several frame mounts (130) and resilient straps (132) are arranged to provide a head frame (124), some frame mounts (130) may not have a corresponding electrode module (100) coupled thereto. It should be understood that some headsets (200) may be configured to accommodate different kinds of electrode systems that have different numbers of and/or arrangements of electrode modules (100), providing a degree of modularity.

Rigid-flex circuit (110) of the present example comprises a flexible circuit (140) that provides flexible connector regions (116, 118), as well as an upper rigid member (112) and a lower rigid member (114). A region (144) of the flexible circuit (140) is sandwiched between upper rigid member (112) and lower rigid member (114) as will be described in greater detail below. Upper rigid member (112) also includes sensing circuitry (120), which includes an amplifier among other components. Electrode modules (100) are thus active in this example. Sensing circuitry (120) may be configured and/or operable in accordance with the teachings of U.S. Pub. No. 2005/0215916, entitled "Active, Multiplexed Digital Electrodes for EEG, ECG, and EMG Applications," published Sep. 29, 2005, the disclosure of which is incorporated by reference herein; and/or in accordance with the teachings of any other document cited herein. Indeed, various ways in which the teachings herein may be combined with the teachings of U.S. Pub. No. 2005/0215916 and/or the teachings of any other document cited herein will be apparent to those of ordinary skill in the art. Alternatively, sensing circuitry (120) may have any other suitable configuration and/or operability. For instance, some versions of circuit board (140) may lack an amplifier, such that electrode modules (100) are not active. Still other suitable ways in which circuit board (140) may be configured, including but not limited to various forms and components of sensing circuitry, will be apparent to those of ordinary skill in the art in view of the teachings herein.

In the present example, conductive ring (106) comprises a tail portion (107) that extends radially outwardly then upwardly. Conductive ring (106) is configured to rest on annular rim (105) of lower clamshell member (104). Capture ring (108) is configured to hold conductive ring (106) against annular rim (105) when electrode module (100) is assembled. Accordingly, annular rim (105) and capture ring (108) cooperate to properly register conductive ring (106) with lower clamshell member (104) and assist in securing conductive ring (106) relative to lower clamshell member (104). Of course, these features are just an example, and various other structures, features, techniques, etc. for registering and/or securing conductive ring (106) relative to lower clamshell member (104) will be apparent to those of ordinary skill in the art in view of the teachings herein. As can also be seen in FIG. 5, upper clamshell member (102) is positionable over rigid-flex circuit (110), capture ring (108), and conductive ring (106) to further secure conductive ring (106) in place by "sandwiching" conductive ring (106) between clamshell members (102, 104). As noted above, a portion of conductive ring (106) is still exposed in the inner diameter of the central opening (160) of the assembled electrode module (100) (e.g., when upper clamshell member (102) is secured to lower clamshell member (104), etc.).

In the present example, conductive ring (106) is also communicatively coupled with sensing circuitry (120) (e.g., through contact via tail portion (107), etc.). In particular, conductive ring (106) is configured to communicate ERP signals to sensing circuitry (120) as will be described in greater detail below. Flexible connector regions (116, 118) include flexible circuitry that is in communication with sensing circuitry (120). Accordingly, it should be understood that either or both flexible connector regions (116, 118) may communicate power and/or signals to and/or from sensing circuitry (120).

Exemplary Rigid-Flex Circuitry Construction

FIGS. 6-11 show rigid-flex circuitry (110) of the present example in greater detail. In particular, FIG. 6 shows assembled electrode modules (100), including upper clamshell member (102). As noted above, flexible connector regions (116, 118) of flexible circuit (140) extend from the ends of each electrode module (100). In particular, and as will be described in greater detail below, flexible connectors (116, 118) are part of a continuous flexible circuit (140) substrate that passes through several electrode modules (100). While this flexible circuit (140) is formed on a single, unitary piece of material, the flexible circuit (140) may be viewed as comprising flexible connector regions (116, 118), which are immediately adjacent to electrode modules (100); and intermediate regions (142), which extend between flexible connector regions (116, 118) of adjacent electrode modules (100). That is, the intermediate region (142) is between the flexible connector region (116) of one electrode module (100) and the flexible connector region (118) of another electrode module (100).

Figure 7:
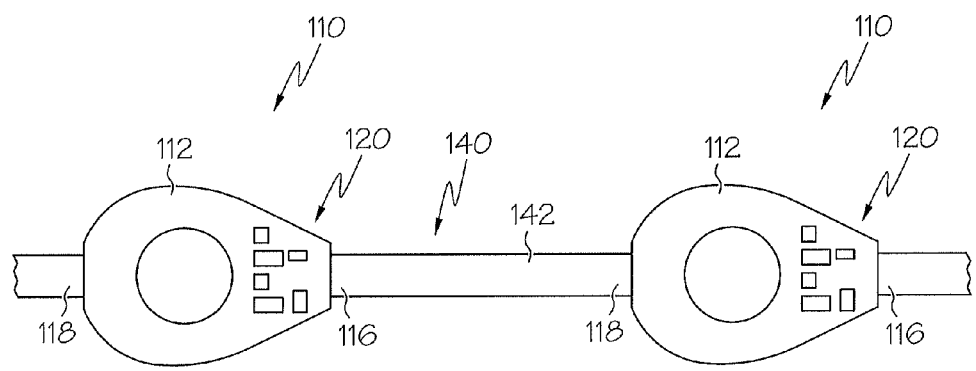
FIG. 7 depicts a top plan view of the electrode components of FIG. 6, with clamshell housing components removed to reveal rigid-flex circuit components.
Figure 8:
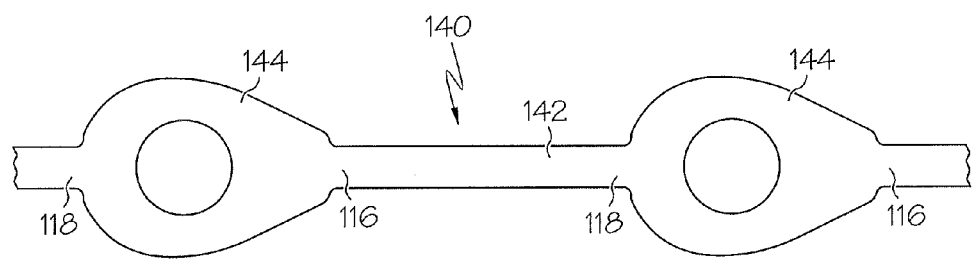
FIG. 8 depicts a top plan view of the electrode components of FIG. 6, with clamshell housing components and rigid circuit components removed to reveal flex circuit components.
Figure 11:
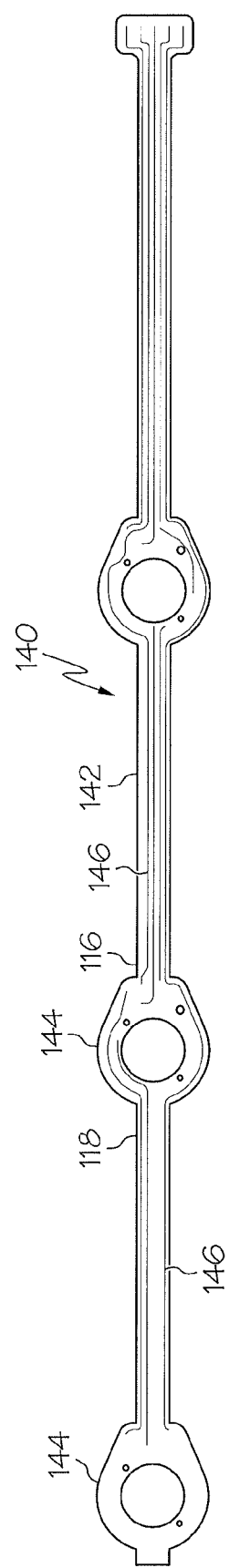
FIG. 11 depicts a top plan view of the electrode components of FIG. 6, with clamshell housing components removed, rigid circuit components removed, and flexible circuit components removed to reveal traces in the flex circuit.

FIG. 7 shows rigid-flex circuitry (110) of the present example, with clamshell members (102, 104) removed. As shown in FIG. 7, upper rigid members (112) are positioned over flexible circuitry (140). Lower rigid members (114) (not shown in FIG. 7) are positioned below flexible circuitry (140). FIG. 8 shows the flexible circuitry (140) of the present example with rigid members (112, 114) removed. As shown, this flexible circuitry (140) is formed on a single, unitary substrate. While FIG. 8 shows only one "strand" of flexible circuitry (140) being formed of a single, unitary substrate, it should be understood that several adjacent strands of flexible circuitry (140) may be formed of a single, unitary substrate. For instance, a single, unitary substrate may be used to form flexible circuitry of the three "strands" providing a substantial equivalent to flexible connectors (50) shown in FIG. 2 and additional flexible circuitry within the control box interface (30) shown in FIG. 2. By way of example only, the single, unitary substrate may comprise one or more alternating layers of plolyamide insulator and copper conductors, among other things. Alternatively, any other suitable material or combination of materials may be used to form the substrate(s) of flexible circuitry (140). It should also be understood that this flexible circuitry (140) may be formed using any suitable techniques, as will be apparent to those of ordinary skill in the art in view of the teachings herein. In the present example, and as shown in FIG. 11, flexible circuitry (140) includes a number of traces (146) (e.g., 5, 8, 10, etc.) along flexible connector regions (116, 118) and intermediate region (142). In other words, each electrode module (100) has a plurality of inputs/outputs, which are provided by traces (146) formed in flexible circuitry (140). Traces (146) may be used to communicate power, data, commands, etc. Of course, any other suitable number of traces (146) and/or inputs/outputs may be used.

In some versions, different electrode modules (100) have their own dedicated traces (146). Dedicated traces (146) for a given electrode module (100) may run along part of the same length of flexible circuitry (140) as dedicated traces (146) for another given electrode module (100). For instance, a set of dedicated traces (146) for one electrode module (100) may be provided on one layer of flexible circuitry (140); while a set of dedicated traces for another electrode module (100) may be provided on another layer of flexible circuitry (140), with both layers extending along a common length of flexible circuitry (140). As another merely illustrative example, dedicated traces (146) for one electrode module (100) may be provided on the same layer of flexible circuitry as dedicated traces (146) for another electrode module (100), such that the separate sets of traces (146) are geometrically parallel on a common layer. In some other versions, different electrode modules (100) may share one or more common traces (146). By way of example only, one or more traces (146) may be used for bus transmissions, such that information associated with different electrode modules (100) may be combined onto a bus and communicated along one or more non-dedicated traces (146) that are in communication with more than one electrode module (100). Various other suitable ways in which traces (146) or other communication features may be used, provided, arranged, etc., will be apparent to those of ordinary skill in the art in view of the teachings herein.

As also shown in FIG. 8, flexible circuitry (140) of the present example includes a sandwiched region (144), which is sandwiched between rigid members (112, 114) when the rigid-flex circuit (110) is complete. The traces (146) (shown only in FIG. 11) of flexible circuit (140) may extend into sandwiched region (144), and may be coupled with sensing circuitry (120) of rigid members (112, 114) in a variety of ways. For instance, rigid members (112, 114) may comprise rigid printed circuit boards, and may have their own traces (not shown). Thus, traces of rigid members (112, 114) may be coupled with traces (146) of sandwiched region (144) of flexible circuitry (140) in a variety of ways. As another merely illustrative example, sensing circuitry (120) may comprise several components having leads that pass through rigid members (112, 114) and that are directly coupled with traces (146) of sandwiched region (144) of flexible circuitry (140) in a variety of ways. In other words, rigid members (112, 114) may simply provide structural support for components of sensing circuitry (120), without necessarily providing traces (146) that act as communicative intermediaries between traces (146) of sandwiched region (144) of flexible circuitry (140) and components of sensing circuitry (120). As yet another merely illustrative alternative, some components of sensing circuitry (120) may be directly coupled with traces (146) of sandwiched region (144), with rigid members (112, 114) merely providing structural support; while rigid members (112, 114) provide traces (not shown) that act as communicative intermediaries between traces (146) of sandwiched region (144) of flexible circuitry (140) and other components of sensing circuitry (120). In any of these versions, sensing circuitry (120) may be coupled with either or both of the rigid members (112, 114) in any suitable fashion. Still other suitable structural and/or communicative relationships between rigid members (112, 114), sensing circuitry (120), and flexible circuitry (140) will be apparent to those of ordinary skill in the art in view of the teachings herein.

It should also be understood that some versions may include sensing circuitry (120) on both rigid members (112, 114); while some other versions may only include sensing circuitry (120) on one of the rigid members (112, 114). Furthermore, some versions may simply have only one rigid member (112), such that the other rigid member (114) is omitted entirely. In still other versions, both rigid members (112, 114) may be omitted entirely. For instance, sensing circuitry (120) and conductive ring (106) may be directly coupled to flexible circuitry (140), if desired.

Figure 9:
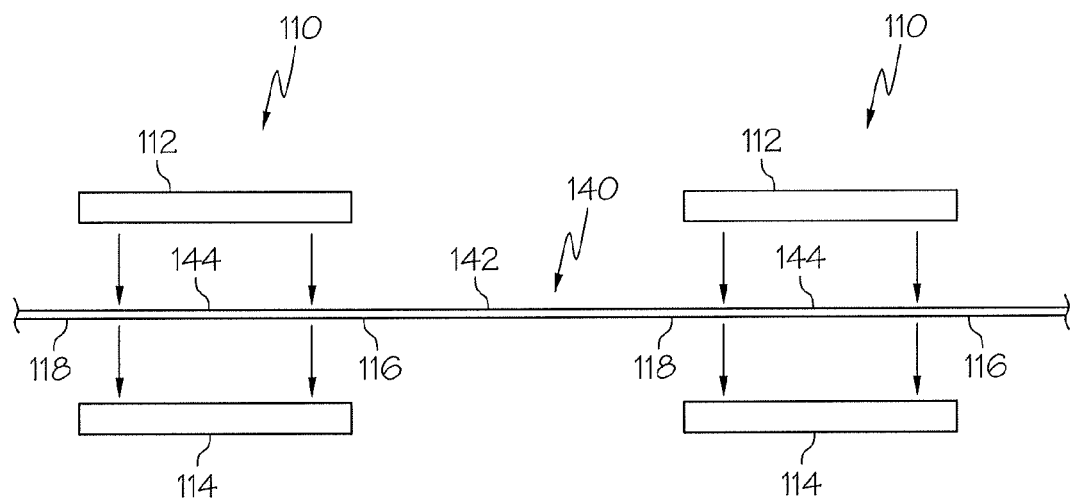
FIG. 9 depicts a side elevational exploded view of the rigid-flex circuit components of FIG. 7, showing the rigid circuit components separated from the flex circuit components.
Figure 10:
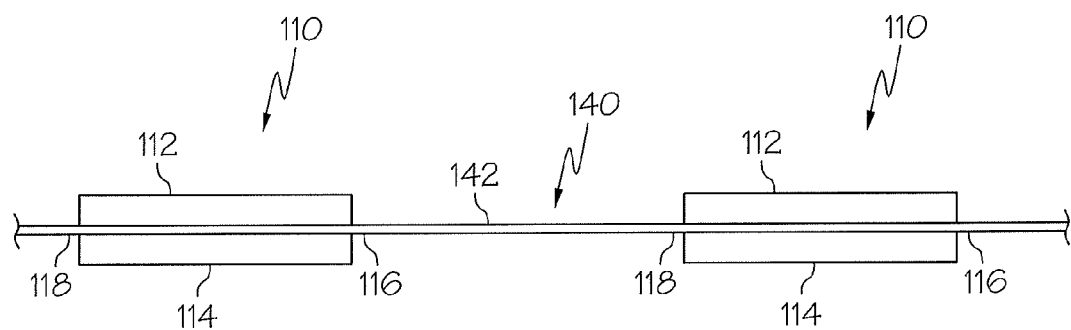
FIG. 10 depicts a side elevational view of the rigid-flex components of FIG. 7, showing the rigid circuit components joined with the flex circuit components.

FIGS. 9-10 also illustrate how a single, unitary flexible circuit substrate is shared by electrode modules (100). While FIGS. 6-10 show two electrode modules (100) sharing a common, unitary flexible circuit substrate, it should be understood that any other suitable number of electrode modules (100) may share a common, unitary flexible circuit substrate. It should be understood that, in some settings, having a single, unitary flexible circuit substrate shared by electrode modules (100) (e.g., physically coupling electrode modules (100), etc.) may provide a relatively high degree of integrity to electrode system (10). For instance, in some other versions, electrode modules (100) may be coupled together by separate discrete strips of flexible circuitry (140). In some such alternative versions, these separate discrete strips of flexible circuitry (140) may be soldered to the adjacent electrode modules (100) or may be plugged into sockets provided by adjacent electrode modules (100). Such soldered or plugged-in connections may present a relatively higher risk of structural and/or electronic failure, particularly if electrode system (10) undergoes physical stress (e.g., electrode modules (100) pulled apart from each other, etc.). By contrast, having a single, unitary flexible circuit substrate that is shared by electrode modules (100) may allow physical stresses (e.g., tensile stress, etc.) to be distributed along the length of the flexible circuit substrate, without such stresses being imposed upon and producing undesirable results at structural weak points along the path of the stress (e.g., solder joints, plug-in couplings, etc.). The construction and use of flexible circuitry (140) having a continuous substrate in rigid-flex circuit (110) may thus provide relatively greater structural and electrical integrity than other configurations, in some settings.

It should also be understood that rigid-flex circuit (110) may be formed in a variety of ways. For instance, rigid members (112, 114) may be formed separately in one or more processes, while flexible circuitry (140) is formed in another process. As shown in FIGS. 9-10, rigid members (112, 114) and flexible circuitry (140) may then be bonded together in any suitable fashion. By way of example only, rigid member (112) may first be bonded to flexible circuitry (140) (or vice-versa); and then rigid member (114) may be bonded to flexible circuitry (140) (or vice-versa). Alternatively, rigid members (112, 114) may be bonded to flexible circuitry (140) substantially simultaneously. As yet another merely illustrative alternative, rigid members (114) may be printed first, then flexible circuitry (140) printed on top of rigid members (114), then rigid members (112) printed on top of flexible circuitry (140), such that rigid-flex circuit (110) is formed in one continuous printing process. Still other suitable ways in which rigid-flex circuit (110) may be formed will be apparent to those of ordinary skill in the art in view of the teachings herein. It should also be understood that, regardless of how rigid-flex circuit (110) is formed, sensing circuitry (120) may be coupled with either or both of rigid members (112, 114) and/or flexible circuitry (140) in a variety of ways.

While the above describes rigid-flex circuit (110) as structurally and communicatively coupling electrode modules (100), it should be understood that control box interface module (230) (see, e.g., FIG. 4) may also include rigid-flex circuitry. For instance, rigid-flex circuitry in control box interface module (230) may be unitary with rigid-flex circuit (110), such that rigid-flex circuitry in control box interface module (230) is structurally and communicatively coupled with rigid-flex circuit (110). As another merely illustrative example, rigid-flex circuitry in control box interface module (230) may be removably coupled with rigid-flex circuit (110). Of course, control box interface module (230) may have any other suitable circuitry configuration and/or construction, including but not limited to those that do not comprise rigid-flex circuitry.

It should also be understood that control box interface module (230) may provide functionality similar to that of control box interface module (30) described above. For instance, control box interface module (230) may include ports (not shown), with which cables (42) may be coupled. The circuitry of control box interface module (230) may be configured to route signals between rigid-flex circuit (110) and cables (42) via such ports. Control box interface module (230) may thus provide a communicative interface between cables (42) and rigid-flex circuit (110). Various suitable components that may be incorporated into control box interface module (230), as well as various suitable features/functionalities of such components, are described in the documents cited herein. By way of example only, control box interface module (230) may be constructed and operable in accordance with the headset "control module 12" teachings of U.S. Pub. No. 2007/0191727 and/or the teachings of any other document cited herein. Still other suitable components that may be incorporated into control box interface module (230) will be apparent to those of ordinary skill in the art in view of the teachings herein.

Exemplary Sensors

Figure 12:
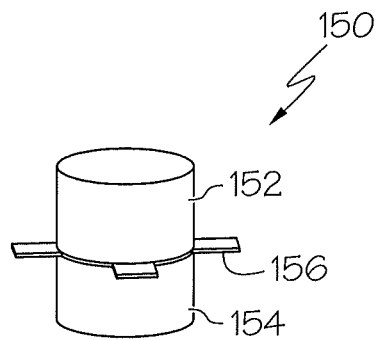
FIG. 12 depicts a perspective view of the sensor of the electrode module of FIG. 5.
Figure 13:
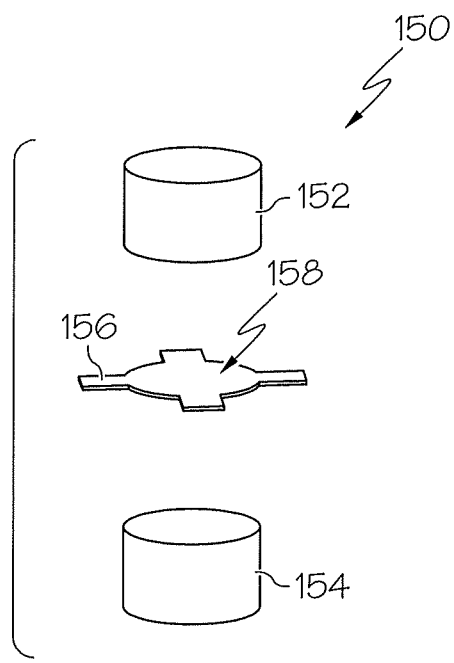
FIG. 13 depicts an exploded view of the sensor of FIG. 12.

As shown in FIGS. 5 and 12-13, electrode system (10) of the present example further includes removable sensors (150). Removable sensors (150) of this example each comprise an insulating upper portion (152), an electrolytic hydrogel lower portion (154), and a conductive center portion (158)

positioned between upper and lower portions (152, 154). Conductive center portion (158) comprises a plurality of outwardly extending conductive tabs (156). Each sensor (150) is configured to be inserted in the central opening (160) of a corresponding electrode module (100) and fit snugly therein. In some settings, each electrode module (100) in an electrode system (10) has an associated removable sensor (150) inserted therein; though some electrode modules (100) may lack an associated electrode module (100) in some settings. Inclined surface (103) of upper clamshell member (102) at the perimeter of opening (160) may facilitate insertion of sensor (150) in opening (160), such as by guiding sensor (150) into opening. Of course, as with other features described herein, inclined surface (103) is merely optional, and may be modified, substituted, supplemented, or omitted as desired.

When removable sensor (150) is inserted in electrode module (100), and the corresponding head frame (124) is secured to a test subject's head, removable sensor (150) is configured such that electrolytic hydrogel lower portion (154) contacts the scalp of the test subject. For instance, sensor (150) may have a height such that hydrogel lower portion (154) protrudes below the bottom of frame mount (130) while insulating upper portion (152) is vertically positioned at or near inclined surface (103) of upper clamshell member (102). Alternatively, sensors (150) may have any other suitable dimensions. Furthermore, depending on the positioning of a given electrode module (100), the associated electrolytic hydrogel lower portion (154) may contact some other part of the test subject's head or body. For instance, hydrogel lower portion (154) may simply contact the hair on the test subject's head; and electrode system (10) may still work properly even if sensors (150) only contact the hair on the test subject's head without necessarily contacting the skin on the test patient's scalp. Due to the electrolytic properties of the electrolytic hydrogel lower portion (154), electrolytic hydrogel lower portion (154) may pick up voltages or signals (e.g., ERP signals, etc.) from the test subject's (e.g., patient's) skin. Electrolytic hydrogel lower portion (154) may collect data without needing to be pasted or glued to the test subject's head, as the hydrogel itself may sufficiently adhere to the subject's head while also allowing removable sensor (150) to be pulled away from the subject's head with relative ease.

As noted above, tabs (156) of the present example are formed as unitary extensions of a conductive member (158) that is disposed between insulating upper portion (152) and electrolytic hydrogel lower portion (154). Conductive member (158) and tabs (156) are configured such that tabs (156) are resiliently biased to assume radially outwardly extending orientations, as shown in FIGS. 5 and 12-13. It should be understood that when sensor (150) is inserted in opening (160) of electrode module (100), tabs (156) contact conductive ring (106), which is at least partially exposed in the inner diameter of opening (160) between clamshell portions (102, 104) when electrode module (100) is assembled. For instance, tabs (156) may resiliently bear against conductive ring (106) when sensor (150) is inserted in opening (160). Such contact between tabs (156) and conductive ring (106) may provide a path for communication from conductive member (158) to conductive ring (106) as described in greater detail below. In addition, elastomeric properties or other properties of insulating upper portion (152) and/or hydrogel lower portion (154) may help retain sensor (150) in opening (160) of electrode module (100). In addition or in the alternative, sensor (150) may be oversized relative to opening (160), such that sensor (150) is snugly or interferingly fit in opening (160). Other ways in which sensor (150) may be substantially retained in opening (160) will be apparent to those of ordinary skill in the art in view of the teachings herein.

Conductive member (158) and tabs (156) may be formed of silver-silver chloride and/or any other suitable material or materials. Conductive ring (106) may also be formed of silver-silver chloride and/or any other suitable material or materials. With conductive member (158) and tabs (156) being in direct contact with electrolytic hydrogel lower portion (154), it should be understood that voltages or signals that are picked up by electrolytic hydrogel lower portion (154) may be further communicated to and through tabs (156). With tabs (156) being in contact with conductive ring (106) when sensor (100) is inserted in opening (160) of electrode module (100), tabs (156) may thus communicate voltages or signals picked up by electrolytic hydrogel lower portion (154) to conductive ring (106), which may in turn communicate such voltages or signals to sensing circuitry (120). An amplifier of sensing circuitry (120) (or elsewhere) may amplify the signal, and other components within sensing circuitry (120) may perform other processing of the signal if desired, and the signal may then be communicated away from electrode module (100) via flexible circuitry in one or both of flexible connector regions (116, 118). The signals may thus ultimately be communicated to control box interface module (320) via flexible circuitry (140) and then on to control box (40) via cable (42).

In some versions, removable sensors (150) comprise HydroDot® Disposable EEG Electrodes or HydroDot® Biosensors by HydroDot, Inc. of Westford, Mass. Various aspects of the HydroDot® Disposable EEG Electrode Application System are discussed in U.S. Pat. No. 5,479,934, entitled "EEG Headpiece with Disposable Electrodes and Apparatus and System and Method for Use Therewith," issued Jan. 2, 1996, which is incorporated by reference herein. Of course, various components of electrode system (10), including but not limited to removable sensors (150), may be configured, modified, and/or operable in accordance with any suitable teachings in U.S. Pat. No. 5,479,934. Indeed, various ways in which the teachings herein may be combined with the teachings of U.S. Pat. No. 5,479,934 will be apparent to those of ordinary skill in the art. It should also be understood that removable sensors (150) are not necessarily required in all versions. For instance, electrode modules (100) may be configured such that they have an electrical interface with the test subject's head and/or some other type of interface with the test subject's head and/or other body part through an injectable gel or in any other suitable fashion.

While sensors (150) of the present example have a substantially cylindraceous shape, it should be understood that sensors (150) may alternatively have any other shape. By way of example only, sensors (150) may have a cubical shape, a right cuboidal shape, a conical shape, a frustoconical shape, a pyramidal shape, a spherical shape, and/or any other suitable shape. Similarly, while conductive rings (150) of the present example have a substantially circular shape, it should be understood that conductive rings (150) may alternatively have any other shape. By way of example only, conductive rings (150) may have a square shape, a rectangular shape, a triangular shape, and/or any other suitable shape. Still other suitable configurations of and relationships between sensors (150) and conductive rings (150) will be apparent to those of ordinary skill in the art in view of the teachings herein.

In the present example, electrode system (10) comprises eight electrode modules (100, 500). As another merely illustrative example, electrode system (10) may comprise twenty three electrode modules (100, 500). Of course, electrode system (10) may alternatively comprise any other suitable number of electrode modules (100, 500). It should also be understood that electrode modules (100, 500) may be arranged in a variety of ways. By way of example only, various suitable arrangements are disclosed in the documents that are cited herein.

Signals obtained using electrode system (10) may be processed in accordance with the teachings of U.S. Pub. No. 2008/0208072, entitled "Biopotential Waveform Data Fusion Analysis and Classification Method," published Aug. 28, 2008, the disclosure of which is incorporated by reference herein and appended hereto. As another merely illustrative example, signals of electrode system (10) may be processed in accordance with the teachings of U.S. Provisional Patent Application Ser. No. 61/381,737, entitled "Biomarker Fusion System and Method," filed Sep. 10, 2010, the disclosure of which is incorporated by reference herein. As yet another merely illustrative example, signals of electrode system (10) may be processed in accordance with the teachings of U.S. Provisional Patent Application Ser. No. 61/381,569, entitled "Electrode System with In-Band Impedance Detection," filed Sep. 10, 2010, the disclosure of which is incorporated by reference herein. Alternatively, signals of electrode system (10) may be processed in any other suitable fashion. In addition, various suitable ways in which electrode system (10) may be used (including but not limited to signal processing) are disclosed in the various documents cited herein. Still other suitable ways in which electrode system (10) may be used will be apparent to those of ordinary skill in the art in view of the teachings herein. It is contemplated that the teachings herein may be incorporated into or otherwise combined with the systems, components, and methods disclosed in the documents cited herein, in numerous ways. Suitable ways in which the teachings herein may be incorporated into or otherwise combined with the teachings of the documents cited herein will be apparent to those of ordinary skill in the art in view of the teachings herein.

Other features of the present electrodes and system will be understood by those of ordinary skill in the art in view of the teachings herein. Furthermore, various modifications, substitutions, supplementations, etc. will be apparent to those of ordinary skill in the art in view of the teachings herein.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An electrode system, comprising:
   (a) a flexible circuit substrate, wherein the flexible circuit substrate comprises a flexible material and traces supported by the flexible material, wherein the traces are configured to provide communication of signals, wherein the flexible circuit substrate further comprises an upper surface and a lower surface;
   (b) a plurality of electrode modules, wherein the flexible circuit substrate extends completely through at least two electrode modules of the plurality of electrode modules such that the at least two electrode modules encompass corresponding portions of the flexible circuit substrate, wherein the electrode modules are positionable at different locations on the head of a test subject, wherein each electrode module comprises a pair of rigid circuit members having sensing circuitry configured to process evoked response potentials (ERPs) of the test subject sensed at the corresponding location on the head of the test subject, wherein the rigid circuit members are layered against the flexible circuit substrate such that the rigid circuit members and the flexible circuit substrate together form a rigid-flex circuit, wherein each pair of rigid circuit members comprises an upper rigid circuit member layered against the upper surface of the flexible circuit substrate and a lower rigid circuit member layered against the lower surface of the flexible surface substrate; and
   (c) a plurality of sensors, wherein each sensor of the plurality of sensors is configured to removably couple with at least one of the plurality of electrode modules, wherein each sensor is configured to sense ERPs from the test subject, wherein each sensor is further configured to communicate sensed ERPs to the associated electrode module, wherein a portion of each sensor is configured to extend outward from the plurality of electrode modules.

2. The electrode system of claim 1, wherein the flexible circuit substrate is configured to provide power to the rigid circuit members via the traces.

3. The electrode system of claim 1, wherein the flexible circuit substrate is configured to communicate signals relating to ERPs from the sensing circuitry along the traces.

4. The electrode system of claim 1, wherein the flexible circuit substrate has an elongate shape defining a length, wherein the upper rigid circuit member and the lower rigid circuit member of each pair of rigid circuit members are both positioned along a common portion of the length of the flexible circuit substrate.

5. The electrode system of claim 1, wherein each sensor of the plurality of sensors comprises at least one tab.

6. The electrode system of claim 1, wherein each sensor of the plurality of sensors comprises an upper and lower portion layered together.

7. The electrode system of claim 1, wherein each electrode module of the plurality of electrode modules defines a substantially central opening, wherein each sensor is positioned within the substantially central opening of the associated electrode module.

8. The electrode system of claim 7, wherein each electrode module further comprises a conductive ring.

9. The electrode system of claim 8, wherein each electrode module further comprises a housing defining the substantially central opening, wherein the conductive ring of each electrode module is at least partially exposed in an inner diameter of the substantially central opening defined by the housing of the associated electrode module.

10. The electrode system of claim 8, wherein each sensor comprises at least one outwardly extending conductive tab, wherein the outwardly extending conductive tab is configured to contact the conductive ring of the associated electrode module.

11. The electrode system of claim 1, wherein each of the electrode modules further comprises an upper clamshell member and a lower clamshell member, wherein the pair of rigid circuit members of each electrode module are positioned between the upper clamshell member and the lower clamshell member of the corresponding electrode module, wherein the upper clamshell member and the lower clamshell member are coupled together.

12. The electrode system of claim 1, wherein the sensing circuitry of each electrode module comprises a corresponding amplifier.

13. The electrode system of claim 1, further comprising a head frame configured to fit on the head of the test subject, wherein the electrode modules are removably coupled with the head frame.

14. The electrode system of claim 1, further comprising a handheld control box in communication with the electrode modules.

15. The electrode system of claim 14, wherein the handheld control box comprises a storage medium storing ERP testing protocols and a processor operable to execute evoked response testing via the electrode modules in accordance with the stored EVP testing protocols.

16. The electrode system of claim 15, wherein the storage medium of the control box is further operable to store results of the evoked response testing.

17. An electrode system, comprising:
(a) a flexible circuit substrate, wherein the flexible circuit substrate comprises a flexible material and traces supported by the flexible material, wherein the traces are configured to provide communication of signals;
(b) a plurality of electrode modules, wherein the flexible circuit substrate extends completely through at least two electrode modules of the plurality of electrode modules such that the at least two electrode modules encompass corresponding portions of the flexible circuit substrate, wherein the electrode modules are positionable at different locations on the head of a test subject, wherein each electrode module comprises at least one rigid circuit member having sensing circuitry configured to process evoked response potentials (ERPs) of the test subject sensed at the corresponding location on the head of the test subject, wherein the rigid circuit members are layered against the flexible circuit substrate such that the rigid circuit members and the flexible circuit substrate together form a rigid-flex circuit; and
(c) a plurality of sensors, wherein each sensor of the plurality of sensors is configured to removably couple with at least one of the plurality of electrode modules, wherein each sensor is configured to sense ERPs from the test subject, wherein each sensor is further configured to communicate sensed ERPs to the associated electrode module, wherein a portion of each sensor is configured to extend outward from the plurality of electrode modules, wherein each sensor of the plurality of sensors comprises at least one tab.

18. An electrode system, comprising:
(a) a flexible circuit substrate, wherein the flexible circuit substrate comprises a flexible material and traces supported by the flexible material, wherein the traces are configured to provide communication of signals;
(b) a plurality of electrode modules, wherein the flexible circuit substrate extends completely through at least two electrode modules of the plurality of electrode modules such that the at least two electrode modules encompass corresponding portions of the flexible circuit substrate, wherein the electrode modules are positionable at different locations on the head of a test subject, wherein each electrode module comprises at least one rigid circuit member having sensing circuitry configured to process evoked response potentials (ERPs) of the test subject sensed at the corresponding location on the head of the test subject, wherein the rigid circuit members are layered against the flexible circuit substrate such that the rigid circuit members and the flexible circuit substrate together form a rigid-flex circuit, wherein each electrode module of the plurality of electrode modules defines a substantially central opening, wherein each electrode module further comprises a conductive ring; and
(c) a plurality of sensors, wherein each sensor is positioned within the substantially central opening of an associated one of the plurality of electrode modules, wherein each sensor of the plurality of sensors is configured to removably couple with the associated electrode module, wherein each sensor is configured to sense ERPs from the test subject, wherein each sensor is further configured to communicate sensed ERPs to the associated electrode module, wherein a portion of each sensor is configured to extend outward from the plurality of electrode modules.

* * * * *